United States Patent [19]
Daftary

[11] Patent Number: 5,810,592
[45] Date of Patent: Sep. 22, 1998

[54] ANATOMICAL RESTORATION DENTAL IMPLANT SYSTEM WITH HEALING ABUTMENT MEMBER AND MATCHING ABUTMENT MEMBER

[76] Inventor: Fereidoun Daftary, 9001 Wilshire Blvd. No. 205, Beverly Hills, Calif. 90211

[21] Appl. No.: 642,889

[22] Filed: May 6, 1996

[51] Int. Cl.⁶ .................................................. A61C 8/00
[52] U.S. Cl. ........................................... 433/173; 433/172
[58] Field of Search .................................. 433/172, 173, 433/174, 175, 176, 201.1

[56] References Cited

U.S. PATENT DOCUMENTS

| | | | |
|---|---|---|---|
| 5,035,619 | 7/1991 | Daftary | 433/173 |
| 5,073,111 | 12/1991 | Daftary | 433/173 |
| 5,145,372 | 9/1992 | Daftary | 433/173 |
| 5,297,963 | 3/1994 | Daftary | 433/172 |
| 5,417,568 | 5/1995 | Giglio | 433/173 |
| 5,431,567 | 7/1995 | Daftary | 433/172 |
| 5,439,380 | 8/1995 | Marlin | 433/173 |
| 5,527,182 | 6/1996 | Willoughby | 433/172 |

*Primary Examiner*—John J. Wilson
*Attorney, Agent, or Firm*—Thomas I. Rozsa; Tony D. Chen

[57] ABSTRACT

An anatomical restoration dental implant system which is attachable to an anatomical restoration dental implant fixture which is embedded into a patient's jawbone. The system includes a healing abutment, a large bolt member, a matching abutment head, and a small bolt member. The healing abutment has an intermediate shoulder for accommodating the gingival tissues which surround the patient's jawbone. The intermediate shoulder has a lingual-side portion which is at a higher level and flush with the top end of the healing abutment, a facial-side portion which is at a lower level and adjacent to the bottom end of the healing abutment, and two opposite interproximal-side portions which are gradually changing from the higher level at the lingual-side portion to the lower level at the facial-side portion.

57 Claims, 7 Drawing Sheets

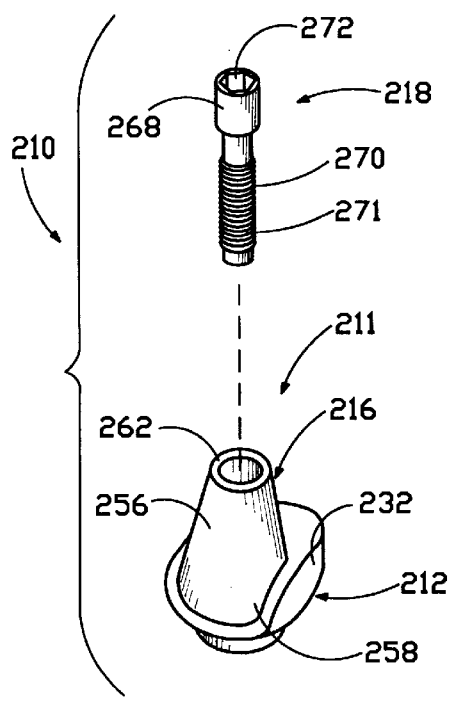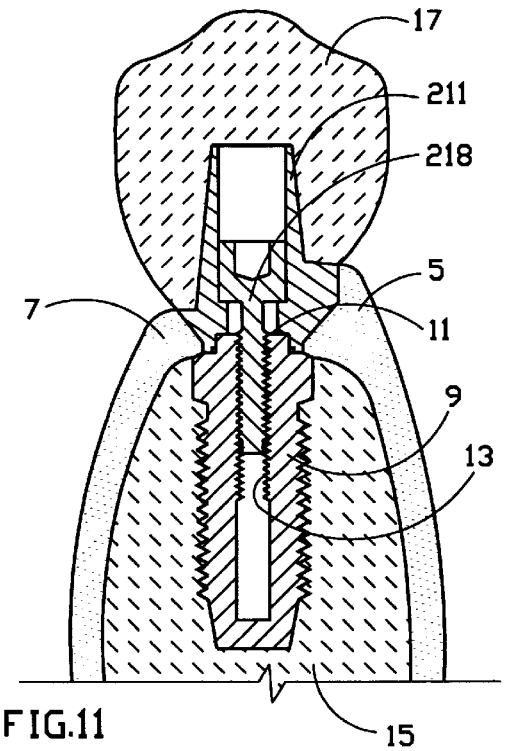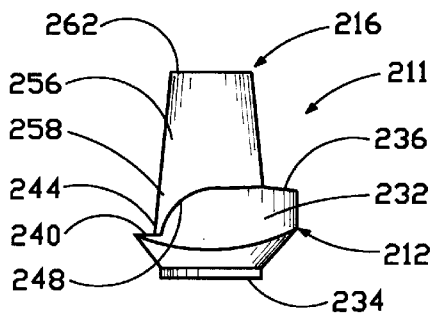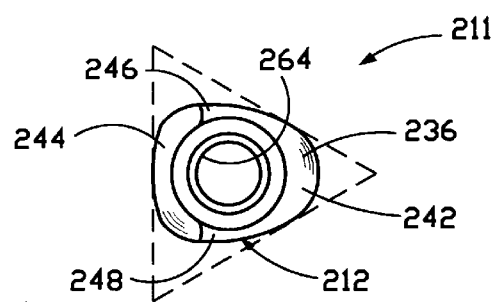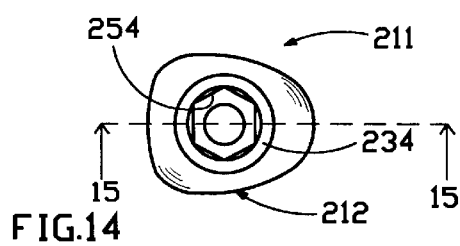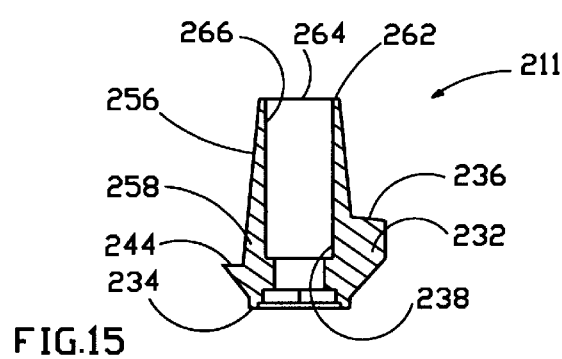

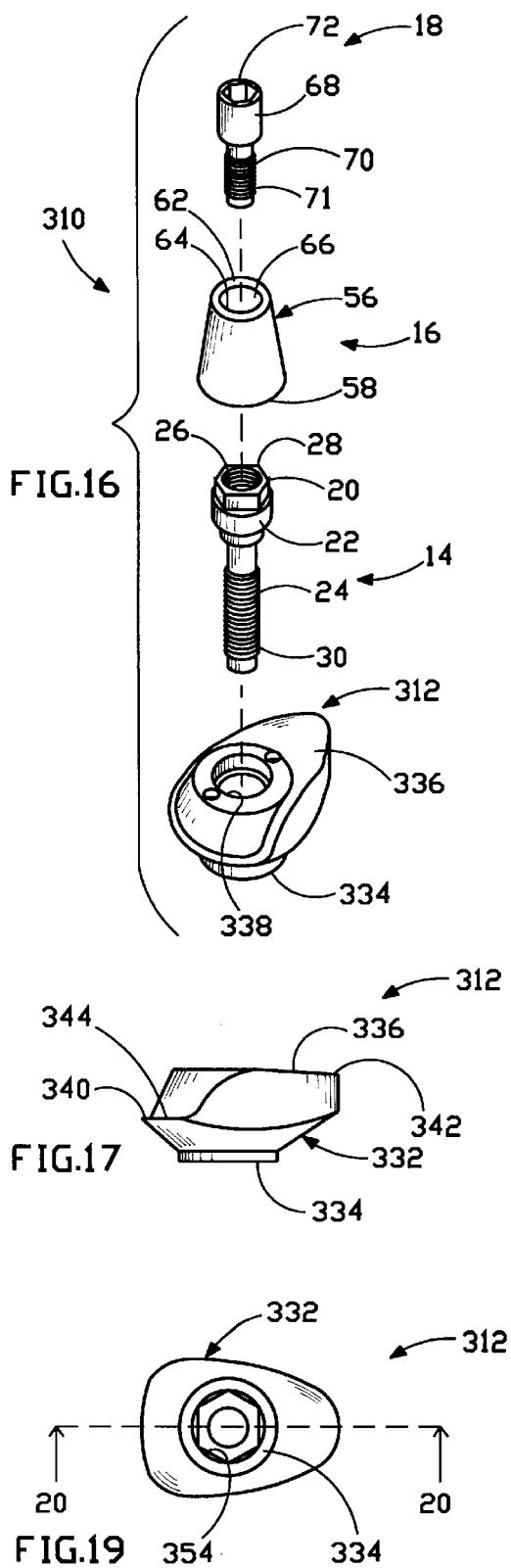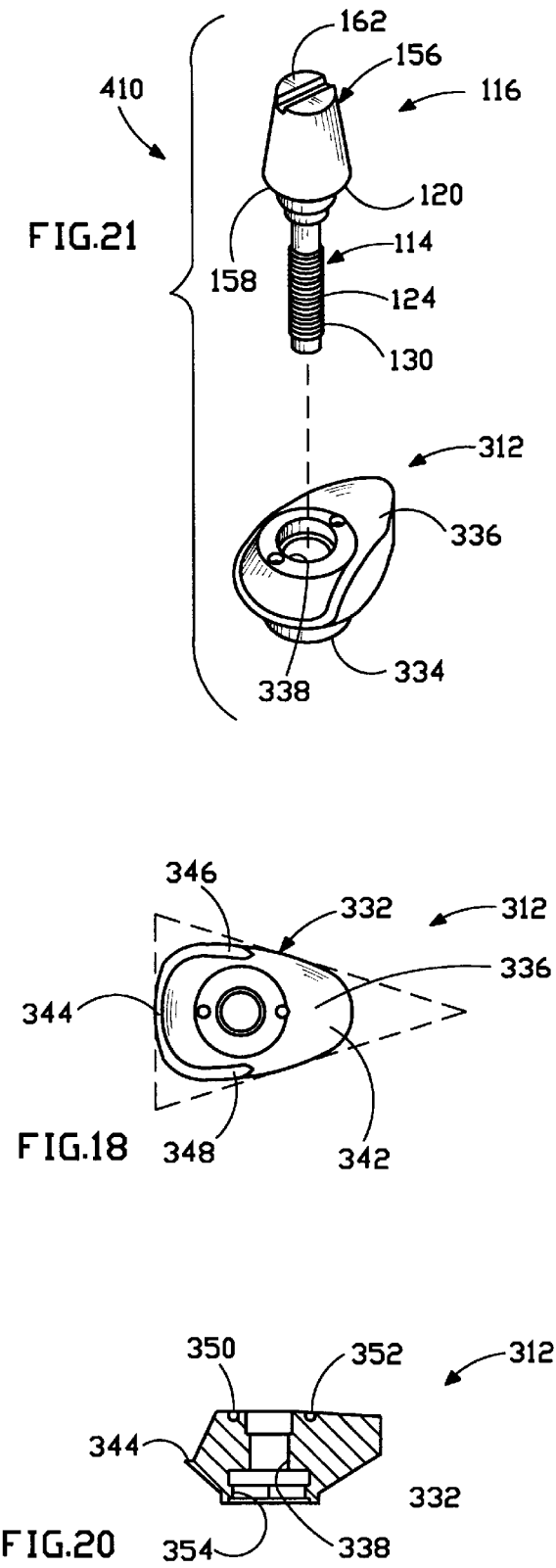

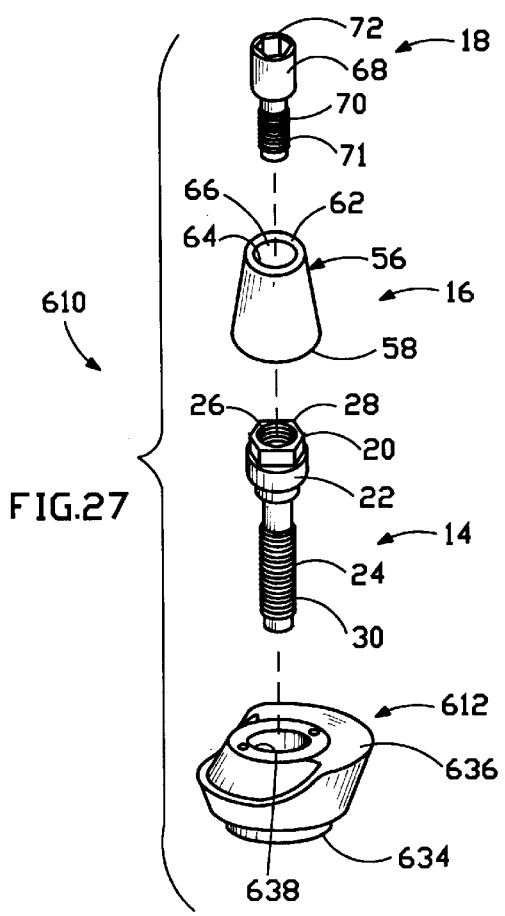
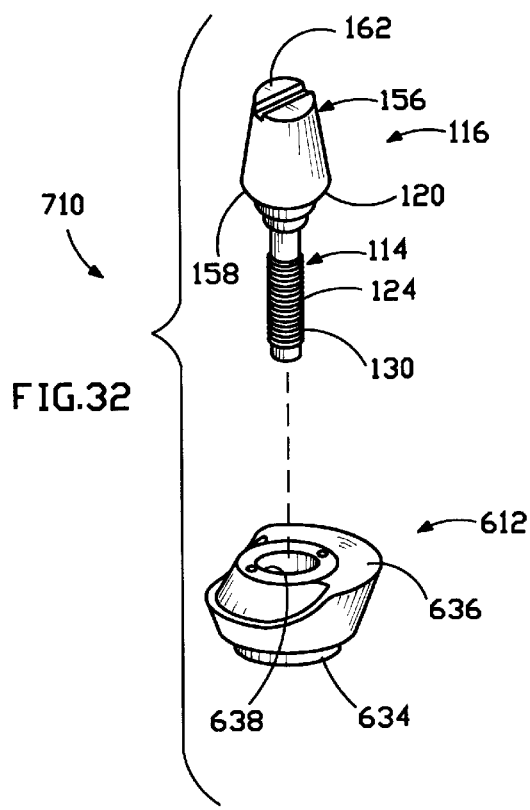
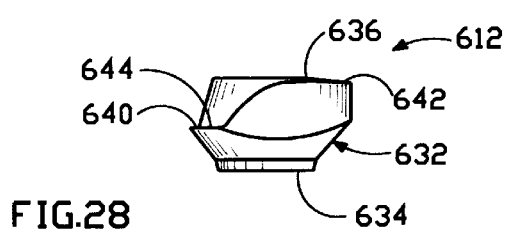
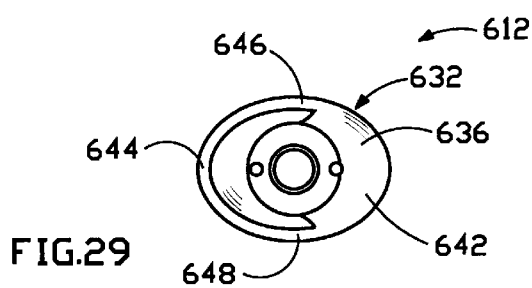
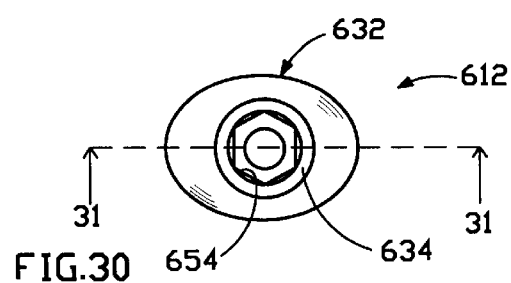
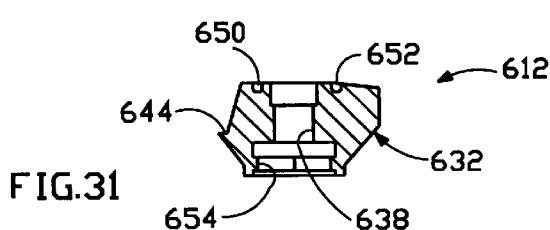

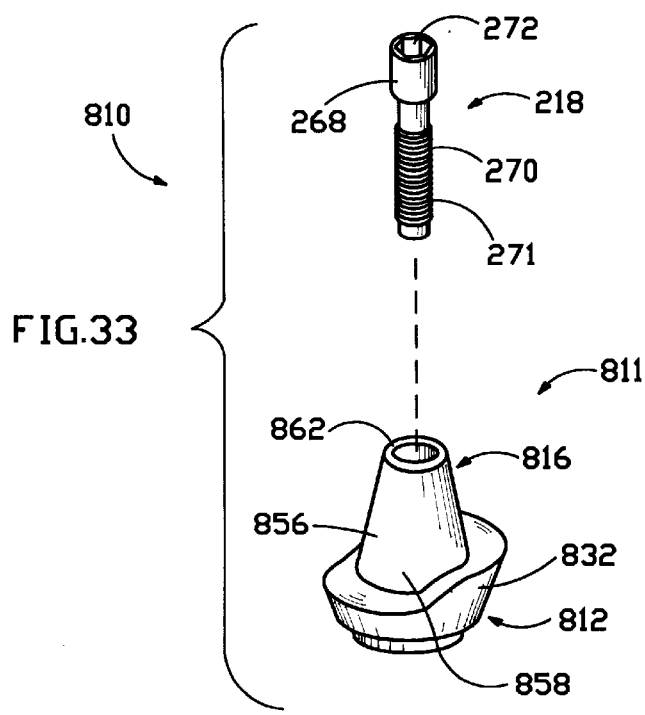
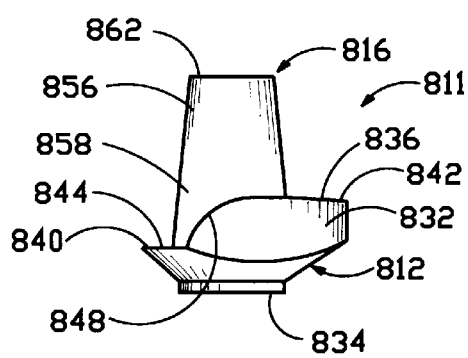
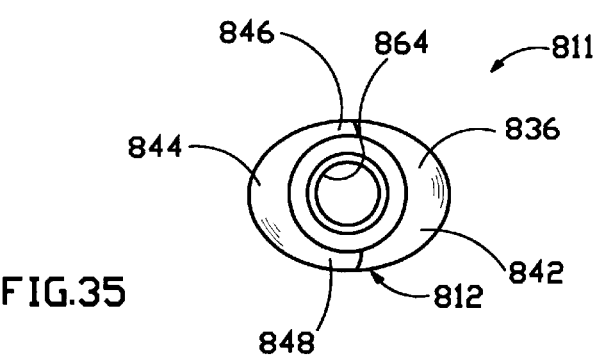
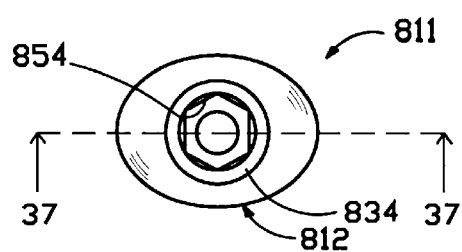
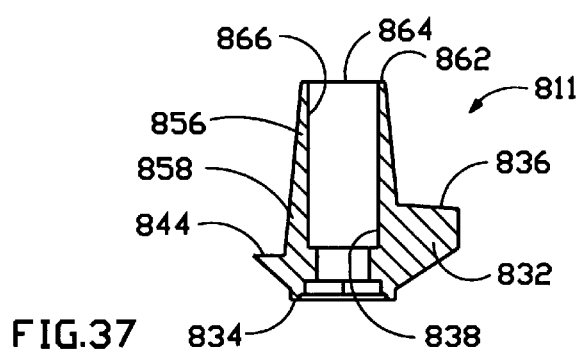

ANATOMICAL RESTORATION DENTAL IMPLANT SYSTEM WITH HEALING ABUTMENT MEMBER AND MATCHING ABUTMENT MEMBER

BACKGROUND OF THE INVENTION

1. Field of the Invention

The present invention generally relates to the field of dental implants and in particular to a system providing a tooth analogue and a gingival tissue healing abutment which results in a restoration having tissue-implant profiles similar to that of a natural tooth and its surrounding gingiva. The present invention also relates to fitting a tooth with a temporary crown and final prosthesis after the initial implant structure has been inserted and the surrounding tissue has healed. More particularly, the present invention relates to the field of an anatomical restoration dental implant system with a contoured healing abutment and a matching abutment head.

2. Description of the Prior Art

The inventor and applicant of the present invention has been practicing anatomical restoration dental implant surgeries for many years and is the patentee of a series of United States Patents related to anatomical restoration dental implant systems which are listed below. While the patentee's prior art anatomical restoration dental implant systems function adequately, the patentee has continuously sought to further improve his products for the dentistry industry.

The following six (6) prior art patents were uncovered in the pertinent field of the present invention:

1. U.S. Pat. No. 5,035,619 issued to Daftary on Jul. 30, 1991 for "Anatomical Restoration Dental Implant System With Improved Healing Cap And Abutment" (hereafter "the '619 Daftary Patent");
2. U.S. Pat. No. 5,073,111 issued to Daftary on Dec. 17, 1991 for "Anatomical Restoration Dental Implant System" (hereafter "the '111 Daftary Patent");
3. U.S. Pat. No. 5,145,372 issued to Daftary on Sep. 8, 1992 for "Anatomical Restoration Dental Implant System With Reinforced Healing Cap And Abutment" (hereafter "the '372 Daftary Patent");
4. U.S. Pat. No. 5,297,963 issued to Daftary on Mar. 29, 1994 for "Anatomical Restoration Dental Implant System With Interlockable Elliptical Healing Cap Assembly And Matching Abutment Member" (hereafter "the '963 Daftary Patent");
5. U.S. Pat. No. 5,417,568 issued to Giglio on May 23, 1995 for "Gingival Contoured Abutment" (hereafter "the Giglio Patent"); and
6. U.S. Pat. No. 5,431,567 issued to Daftary on Jul. 11, 1995 for "Anatomical Restoration Dental Implant System With Interlockable Various Shaped Healing Cap Assembly And Matching Abutment Member" (hereafter "the '567 Daftary Patent").

The '629 Daftary Patent discloses an assembly of a two-piece healing cap and a matching abutment for improving the healing process of the gingival tissue.

The '111 Daftary Patent discloses an anatomical restoration dental implant system for implanting a tooth analogue in the alveolus of the jawbone. The system comprises an implantable fixture implanted through an opened gingival tissue into the alveolus of the jawbone. A cover screw is used for sealing the hollow of the implant fixture during the time the jawbone is growing about the implant fixture. After osseointegration of the implant fixture, the gingiva is reopened and the cover screw is removed and replaced by a healing cap.

The '372 Daftary Patent discloses a reinforced assembly of a two-piece healing cap and a matching abutment. The two-piece healing cap configurations are designed to prevent the unnecessary damage or delay to the healing of the gingival tissues.

The '963 Daftary Patent discloses an anatomical restoration dental implant system with an interlockable elliptical healing cap assembly and a matching abutment member for supporting a tooth analogue with an elliptical root. The healing cap assembly comprises an integral bolt member which has a widened head segment and an elongated shaft segment. The healing cap assembly also comprises a healing cap member which has a divergent body with a larger elliptical end. The healing cap member and the bolt member are interlockable by threading the proximal section of the shaft segment of the bolt member into the distal section of the interior bore of the healing cap member.

The Giglio Patent discloses a gingival contoured abutment for a dental implant that is contoured to follow the gingival margin. The dental prosthesis creates gingival contours surrounding an implant prosthesis which imitate the gingival contours around natural teeth as well as around conventional fixed prosthodontics restorations. The prosthesis comprises an implant fixture and an abutment attached to the fixture. The abutment is scalloped or contoured such that there is a raised ridge on the interproximal side of the abutment. A cylinder is conventionally attached to the abutment, where a conventional porcelain restoration is mounted on the cylinder. The scalloped portion of the abutment must fall on the interproximal surface of the restoration regardless of the implant fixture orientation.

The '567 Daftary Patent discloses an anatomical restoration dental implant system with an interlockable various shaped healing cap assembly and a matching abutment member for supporting a tooth analogue with a rounded triangle shaped root. The healing cap assembly comprises an integral bolt member and a healing cap member, which are interlockable. The matching abutment has a bolt segment which is identical to the bolt member of the healing cap assembly, and a frusto-conical shaped head segment. The large end of the frusto-conical shaped head segment of the abutment member is circular shaped and smaller than the rounded triangle shaped end of the healing cap member, such that when the abutment member is attached to the healing cap member, a rounded triangle shaped shoulder is created for matching perfectly with the rounded triangle shaped root of the tooth analogue.

It is always desirable to improve the anatomical restoration dental implant system so that it can provided a contour more nearly approximating that of a natural tooth and its surrounding tissue, and an implant root and gingival tissue interface that enhances the resistance to bacterial infection.

SUMMARY OF THE INVENTION

The present invention is an anatomical restoration dental implant system which is attachable to an anatomical restoration dental implant fixture which is embedded into a patient's jawbone and has an exposed open end with inner screw threads.

In the preferred embodiment of the present invention, the anatomical restoration dental implant system can be made from four pieces: the four piece design consists of a healing abutment; a large bolt member; a matching abutment head; and a small bolt member.

In an alternative embodiment of the present invention, the anatomical restoration dental implant system can be made from two pieces: the two piece design consists of a healing abutment and an integral matching abutment member which has a proximal bolt portion and a generally frusto-conical shaped distal head portion for supporting a tooth analogue.

In another alternative embodiment of the present invention, the anatomical restoration dental implant system can be made from a unitary piece which has a healing abutment portion and a matching abutment portion.

In general, the uniqueness of the present invention is that the healing abutment has an intermediate shoulder for accommodating the gingival tissues which surround the patient's jawbone. The intermediate shoulder has a lingual-side portion which is at a higher level and flush with the top end of the healing abutment, a facial-side portion which is at a lower level and adjacent to the bottom end of the healing abutment, and two opposite interproximal-side portions which are gradually changing from the higher level at the lingual-side portion to the lower level at the facial-side portion.

Other shaped healing abutments are needed to better fit with the root of a tooth analogue. As shown in the '567 Daftary Patent, teeth are different. It can be seen from FIG. 18 of the '567 Daftary Patent that roots of the bicuspids and cuspids are generally elliptical shaped, accordingly the elliptical shaped healing abutments are used for the bicuspids and the cuspids. It can also be seen from FIG. 18 of the '567 Daftary Patent that roots of the incisors are generally rounded triangular shaped. More particularly, the roots of the two upper central incisors are more rounded equilateral triangle shaped, whereas the two upper lateral incisors and the four lower incisors are more rounded isosceles triangle shaped, accordingly the rounded equilateral triangle shaped healing abutments are used for the upper central incisors, while the rounded isosceles triangle shaped, healing abutments are used for the two upper lateral incisors and the four lower incisors.

It is therefore an object of the present invention to provide healing abutments with various shaped top surfaces, which can provide a better match with the various shaped tooth analogues.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 10 is an exploded perspective view of another alternative a embodiment of the present invention anatomical restoration dental implant system, showing an integral member with a rounded equilateral triangle shaped healing abutment portion and a matching abutment portion;

FIG. 11 is an enlarged cross-sectional view of the present invention anatomical restoration dental implant system shown in FIG. 10, showing the integral member for supporting a tooth analogue;

FIG. 12 is a side elevational view of the present invention integral member shown in FIG. 10;

FIG. 13 is a top plan view of the present invention integral member shown in FIG. 10;

FIG. 14 is a bottom plan view of the present invention integral member shown in FIG. 10;

FIG. 15 is a cross-sectional view taken along line 15—15 of FIG. 14;

FIG. 16 is an exploded perspective view of still another alternative embodiment of the present invention anatomical restoration dental implant system, showing a four piece design;

FIG. 17 is a side elevational view of the present invention rounded isosceles triangle shaped healing abutment shown in FIG. 16;

FIG. 18 is a top plan view of the present invention rounded isosceles triangle shaped healing abutment shown in FIG. 16;

FIG. 19 is a bottom plan view of the present invention rounded isosceles triangle shaped healing abutment shown in FIG. 16;

FIG. 20 is a cross-sectional view taken along line 20—20 of FIG. 19;

FIG. 21 is an exploded perspective view of a further alternative embodiment of the present invention anatomical restoration dental implant system, showing a two piece design;

FIG. 27 is an exploded perspective view of still further alternative embodiment of the present invention anatomical restoration dental implant system, showing a four piece design;

FIG. 28 is a side elevational view of the present invention elliptical shaped healing abutment shown in FIG. 27;

FIG. 29 is a top plan view of the present invention elliptical healing abutment shown in FIG. 27;

FIG. 30 is a bottom plan view of the present invention elliptical shaped healing abutment shown in FIG. 27;

FIG. 31 is a cross-sectional view taken along line 31—31 of FIG. 30;

FIG. 32 is an exploded perspective view of an additional alternative embodiment of the present invention anatomical restoration dental implant system, showing a two piece design;

FIG. 33 is an exploded perspective view of another additional alternative embodiment of the present invention anatomical restoration dental implant system, showing an integral member with an elliptical healing abutment portion and a matching abutment portion;

FIG. 34 is a side elevational view of the present invention integral member shown in FIG. 33;

FIG. 35 is a top plan view of the present invention integral member shown in FIG. 33;

FIG. 36 is a bottom plan view of the present invention integral member shown in FIG. 33; and FIG. 37 is a cross-sectional view taken along line 37—37 of FIG. 36.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
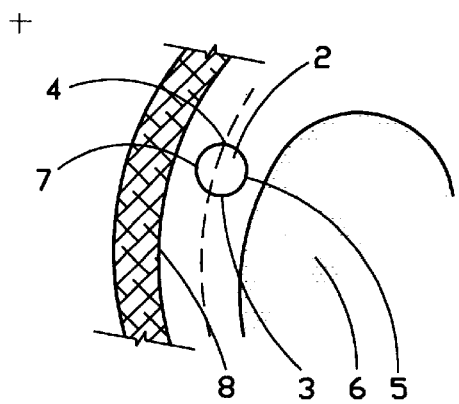
FIG. 1 is an illustrative diagram of a patient's oral cavity.

Referring to FIG. 1, there is shown an illustrative diagram of a patient's oral cavity. In natural teeth, the gingival tissues around each tooth 2 comprises opposite interproximal sides (mesial and distal) 3 and 4, a lingual side 5 which is adjacent to the tongue 6, and a facial side 7 which is adjacent to the interior surface 8 of the patient's cheek. The gingival tissue at the lingual side 5 is at a higher level than the gingival tissue of the facial side 7, while the gingival tissues on the interproximal sides 4 and 5 are gradually decreasing from the higher level to a level which communicates with the facial side 7.

Figure 2:
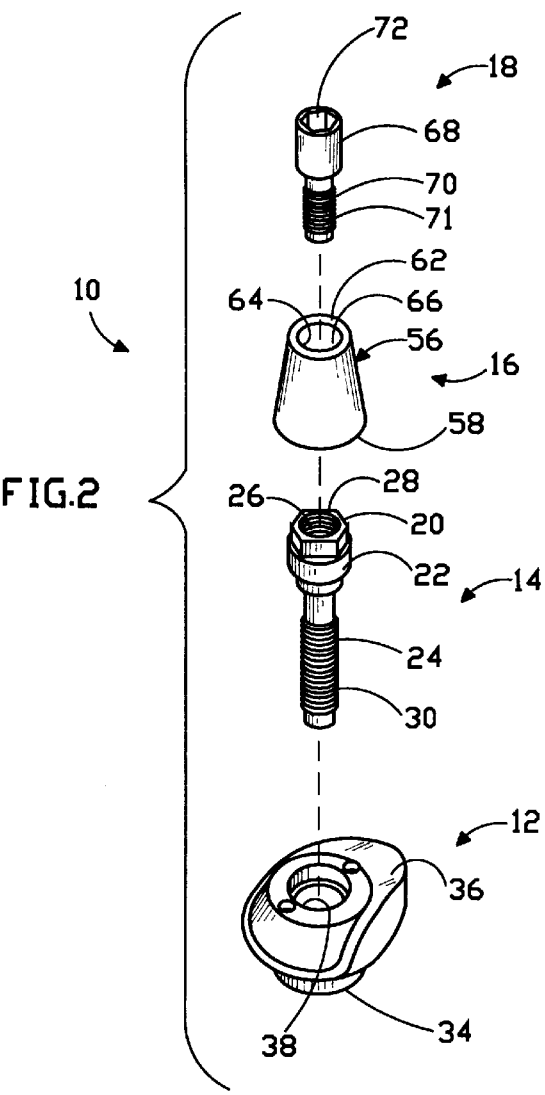
FIG. 2 is an exploded perspective view of the preferred embodiment of the present invention anatomical restoration dental implant system, showing a four piece design.
Figure 3:
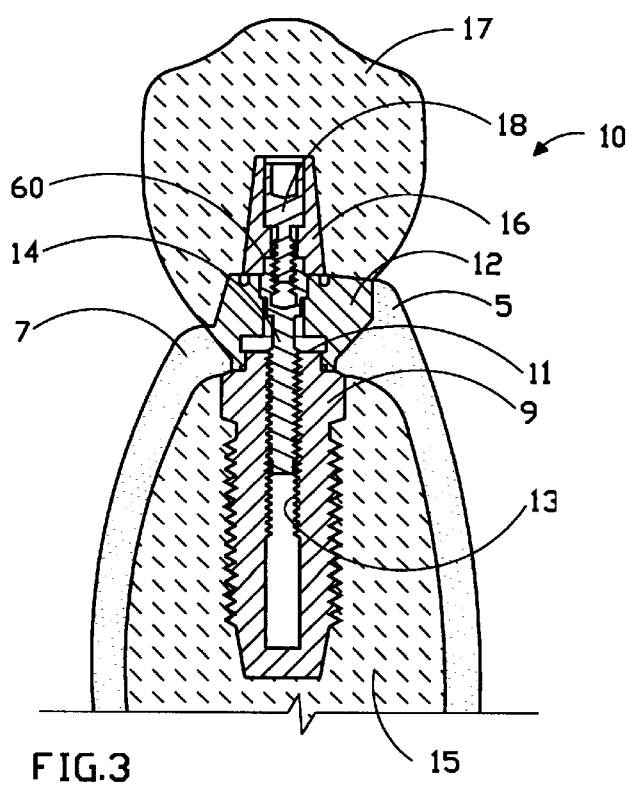
FIG. 3 is an enlarged cross-sectional view of present invention anatomical restoration dental implant system shown in FIG. 2, showing the matching abutment head which is secured on the healing abutment for supporting a tooth analogue.
Figure 4:
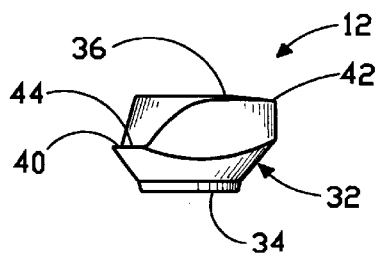
FIG. 4 is a side elevational view of the present invention rounded equilateral triangle shaped healing abutment shown in FIG. 2.

Referring to FIG. 2, there is shown an exploded perspective view of the present invention anatomical restoration dental implant system 10 which is attachable to an anatomical restoration dental implant fixture 9 which is embedded into a patient's jawbone 15 and has an exposed open end 11 with inner screw threads 13 (see FIG. 3). The dental implant system 10 can be made from four pieces: the four piece design consists of a rounded equilateral triangle shaped healing abutment 12; a large bolt member 14; a matching abutment head 16; and a small bolt member 18.

Referring to FIGS. 4 through 7, there is shown at 12 the rounded equilateral triangle shaped healing abutment of the present invention. The healing abutment 12 has a generally divergent body 32 which has a smaller proximal end 34 and a larger distal end 36. The smaller proximal end 34 is circular shaped, whereas the larger distal end 36 is rounded equilateral triangle shaped. The divergent body 32 also has a stepped interior bore 38 which extends from the distal end 36 to the proximal end 34. The divergent body 32 further has an intermediate shoulder 40 for accommodating the gingival tissues 5 and 7 (see FIG. 3) which surround the patient's jawbone 15. The intermediate shoulder 40 has a lingual-side portion 42 which is at a higher level and flush with the distal end 36 of the divergent body 32, a facial side portion 44 which is at a lower level and adjacent to the proximal end 34 of the divergent body 32, and two opposite interproximal-side portions 46 and 48 which are gradually changing from the higher level at the lingual-side portion 42 to the lower level at the facial-side portion 44. As shown in FIGS. 4–7 the lingual-side portion 42 of the shoulder has a greater surface area than the facial-side portion 44 of the shoulder. The larger distal end 36 of the healing abutment 12 further comprises two opposite indents 50 and 52 which are adaptable with a dental forceps for orienting the healing abutment 12.

Figure 5:
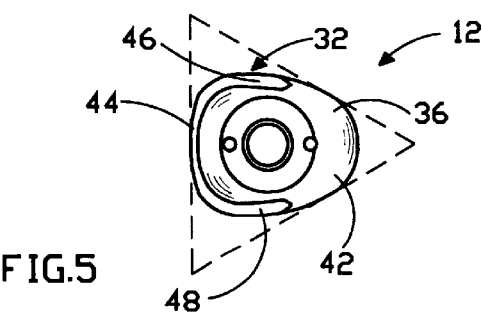
FIG. 5 is a top plan view of the present invention rounded equilateral triangle shaped healing abutment shown in FIG. 2.

Particularly referring to FIG. 5, an equilateral triangle circumscribing the distal end 36 of the healing abutment 12 is shown in dotted lines to illustrate that the distal end 36 of the healing abutment 12 has a rounded equilateral triangle shape.

Referring to FIG. 3, there is shown a cross-sectional view of the present invention anatomical restoration dental implant system 10 which shows the matching abutment head 16 which is secured on the healing abutment 12 for supporting a tooth analogue 17. There is a mating interface at the exposed end 11 of the implant fixture 9 and a complementary mating interface at the smaller proximal end 34 of the healing abutment 12 for orienting and aligning the healing abutment 12. The mating interface at the exposed end 11 of the implant fixture 9 is a hexagonal lip and the complementary mating interface at the smaller proximal end 34 of the healing abutment 12 is a hexagonal recess 54.

Figure 6:
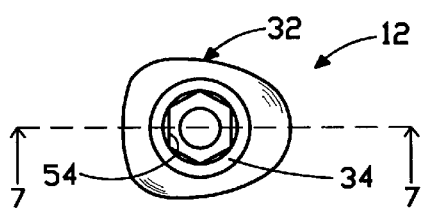
FIG. 6 is a bottom plan view of the present invention rounded equilateral triangle shaped healing abutment shown in FIG. 2.
Figure 7:
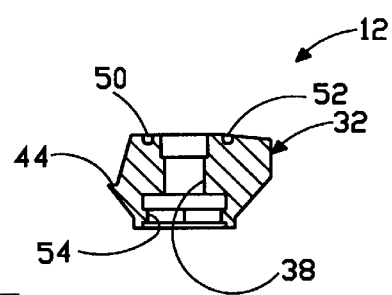
FIG. 7 is a cross-sectional view taken along line 7—7 of FIG. 6.

It will be appreciated that at the smaller proximal end 34 of the healing abutment 12 is not limited to the hexagonal recess 54 as shown in FIG. 6. It is also within the spirit and scope of the present invention to utilize a circular recess provided at the smaller proximal end 34 of the healing abutment 12 for matching a complementary circular lip at the exposed end of the dental implant fixture.

Referring to FIGS. 2 and 3, the large bolt member 14 has a widened head segment 20, an elongated shaft segment 24 and a circular shaped shoulder segment 22 which is located between the head segment 20 and the shaft segment 24. The widened head segment 20 is hexagonal shaped to accommodate a driving tool for rotating the bolt member 14. The head segment 20 has an exposed open end 26 with inner screw threads 28. The shaft segment 24 has outer screw threads 30. The shaft segment 24 is longer than the interior bore 38 of the healing abutment 12, such that after the shaft segment 24 extends through the interior bore 38 of the healing abutment 12 from the distal end 36 of the healing abutment 12, there is still a substantial portion of the outer screw threads 30 of the shaft segment 24 which can be threadably engaged with the implant fixture 9 for fastening the healing abutment 12 to the exposed end 11 of the implant fixture 9. When the bolt member 14 is secured to the implant fixture, the head segment 20 extends about the distal end 36 of the healing abutment 12.

The matching abutment head 16 is used for supporting a tooth analogue 17 and is designed very similar to patentee's prior abutment heads. The abutment head 16 has a generally frusto-conical shaped body 56. The frusto-conical shaped body 56 has a larger proximal end 58 with a widened socket 60, a smaller distal end 62 with a circular opening 64, and a stepped interior bore 66 extending from the widened socket 60 to the circular opening 64. The larger proximal end 58 is installed on the distal end 36 of the healing abutment 12, such that the widened socket 60 matches the head segment 20 of the larger bolt member 14. The widened socket 60 of the frusto-conical shaped body 56 is generally a hexagonal recess.

The small bolt member 18 has a circular shaped head segment 68 and a shaft segment 70 with outer screw threads 71. The head segment 68 has an internal opening 72 for adapting a driving tool such that the small bolt member 18 extends through the interior bore 66 of the abutment head 16 from the circular opening 64. The outer screw threads 71 of the small bolt member 18 are threadedly engaged with the inner screw threads 28 of the exposed open end 26 of the head segment 20 of the large bolt member 14, thereby securing the abutment head 16 to the healing abutment 12.

The facial-side portion 44 of the healing abutment 12 accommodates the contour of the gingival tissue 7 at the facial side of the patient. The lingual-side portion 42 of the healing abutment 12 accommodates the contour of the gingival tissue 5 at the lingual side of the patient.

It is noted that the rounded equilateral triangle shaped distal end 36 of the healing abutment 12 is used for matching the rounded equilateral triangle shaped root of the tooth analogue for the upper central incisors. This rounded equilateral triangle shaped distal end 36 is one of the unique features of the present invention because it solves the problem of mismatching between the roots of the central incisors and the round or circular abutment shoulder provided by prior art dental implant systems. The smaller profile of the present invention rounded equilateral triangle distal end also allows two tooth analogues to be positioned at a desired or required close distance.

Figure 8:
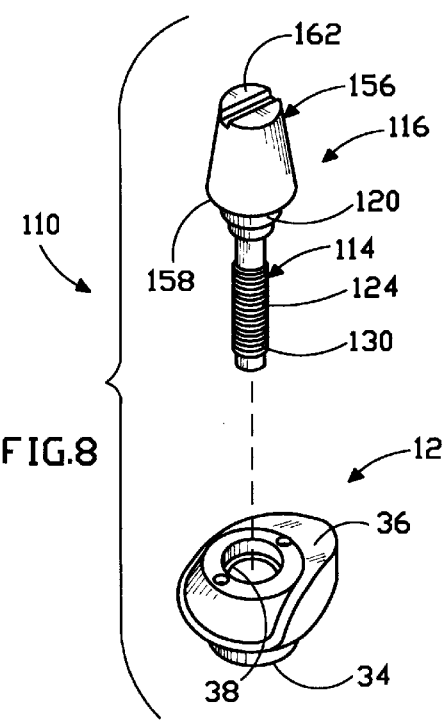
FIG. 8 is an exploded perspective view of an alternative embodiment of the present invention anatomical restoration dental implant system, showing a two piece design.
Figure 9:
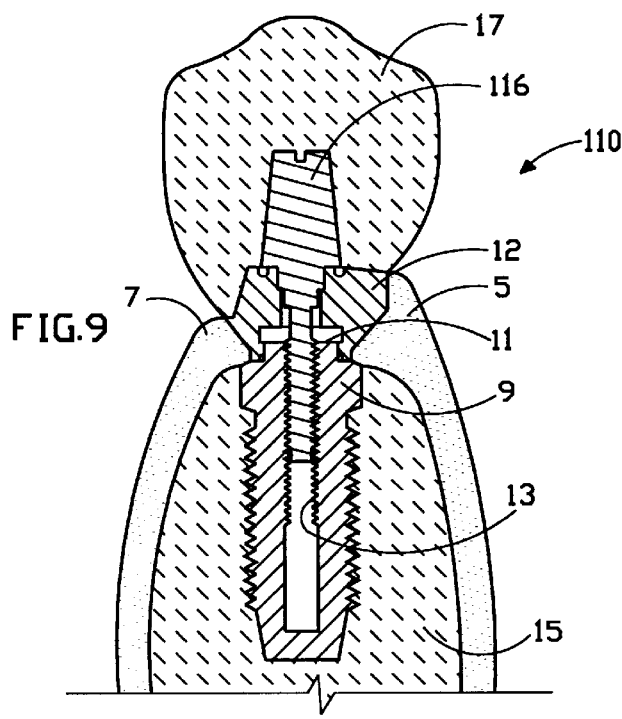
FIG. 9 is an enlarged cross-sectional view of the present invention anatomical restoration dental implant system shown in FIG. 8, showing the abutment member which is secured on the healing abutment for supporting a tooth analogue.

Reference is now made to FIGS. 8 and 9, where FIG. 8 is an exploded view of an alternative embodiment of the present invention anatomical restoration dental implant system 110, and FIG. 9 is shown a cross-sectional view of the present invention anatomical restoration dental implant system 110. In this embodiment, the healing abutment 12 is the same as the preceding embodiment, and the description thereof will not be repeated.

An integral matching abutment member 116 has a proximal bolt portion 114 and a generally frusto-conical shaped distal head portion 156 for supporting a tooth analogue 17. The proximal bolt portion 114 has a head segment 120 and an elongated shaft segment 124. The shaft segment 124 has outer screw threads 130. The shaft segment 124 is longer than the interior bore 38 of the healing abutment 12, such that after the shaft segment 124 extends through the interior bore 38 of the healing abutment 12 from the distal end 36 of the healing abutment 12, there is still a substantial portion of the outer screw threads 130 of the shaft segment 124 which can be threadably engaged with the implant fixture 9 for fastening the healing abutment 12 to the exposed end 11 of the implant fixture 9. The frusto-conical shaped distal head portion 156 has a larger proximal end 158 and a smaller distal end 162. The larger proximal end 158 is integrally connected to the head segment 120 of the proximal bolt portion 114.

Referring to FIG. 10, there is shown an exploded perspective view of another alternative embodiment of the present invention anatomical restoration dental implant system 210 which is attachable to an anatomical restoration dental implant fixture 9 which is embedded into a patient's jawbone 15 and has an exposed open end 11 with inner screw threads 13 (see FIG. 3). The dental implant system 210 can be made from an integral member 211.

Referring to FIGS. 12 through 15, there is shown at 211 the integral member. The integral member 211 comprises a healing abutment portion 212 and a matching abutment head portion 216. The healing abutment portion 212 has a generally divergent body 232 which has a smaller proximal end 234 and a larger distal end 236. The smaller proximal end 234 is circular shaped, whereas the larger distal end 236 is rounded equilateral triangle shaped. The divergent body 232 also has a stepped interior bore 238 which extends from the distal end 236 to the proximal end 234. The divergent body 232 further has an intermediate shoulder 240 for accommodating the gingival tissues 5 and 7 (see FIG. 11) which surround the patient's jawbone 15. The intermediate shoulder 240 has a lingual-side 242 which is at a higher level and flush with the distal end 236 of the divergent body 232, a facial-side 244 which is at a lower level and adjacent to the proximal end 234 of the divergent body 232, and two opposite interproximal-sides 246 and 248 which are gradually changing from the higher level to the lower level. There is a mating interface at the exposed end 11 of the implant fixture 9 and a complementary mating interface at the smaller proximal end 234 of the healing abutment portion 212 for orienting and aligning the integral member 211. The mating interface at the exposed end 11 of the implant fixture 9 is a hexagonal lip and the complementary mating interface at the smaller proximal end 234 of the healing abutment portion 212 is a hexagonal recess 254.

It will be appreciated that at the smaller proximal end 234 of the healing abutment portion 212 is not limited to the hexagonal recess 254 as shown in FIG. 14. It is also within the spirit and scope of the present invention to utilize a circular recess provided at the smaller proximal end 234 of the healing abutment portion 212 for matching a complementary circular lip at the exposed end of the dental implant fixture.

Particularly referring to FIG. 13, an equilateral triangle circumscribing the distal end 236 of the healing abutment portion 212 is shown in dotted lines to illustrate that the distal end 236 of the healing abutment portion 212 has a rounded equilateral triangle shape.

Referring to FIGS. 10 through 15, the matching abutment head portion 216 is used for supporting a tooth analogue 17. The abutment head portion 216 has a generally frusto-conical shaped body 256. The frusto-conical shaped body 256 has a larger proximal end 258 which is integrally connected to the larger distal end 236 of the healing abutment portion 212, a smaller distal end 262 with a circular opening 264, and a stepped interior bore 266 which extends from the circular opening 264 to the smaller proximal end 234 of the healing abutment portion 212.

Referring to FIGS. 10 and 11, there is shown at 218 a bolt member. The bolt member 218 has a circular shaped head segment 268 and an elongated shaft segment 270 with outer screw threads 271. The head segment 268 has an internal opening 272 for adapting a driving tool. The bolt member 218 extends through the interior bores 238 and 266 of the healing abutment portion 212 and the abutment head portion 216 respectively from the circular opening 264 of the abutment head portion 216. The outer screw threads 271 of the shaft segment 270 are threadedly engaged with the inner screw threads 13 of the exposed open end 11 of the implant fixture 9 for fastening the integral member 211 to the implant fixture 9.

Referring to FIGS. 12 through 15, the facial-side 244 of the healing abutment portion 212 accommodates the contour of the gingival tissue 7 at the facial side of the patient. The lingual-side 242 of the healing abutment 212 accommodates the contour of the gingival tissue 5 at the lingual side of the patient.

It is also noted that the rounded equilateral triangle shaped distal end 236 of the healing abutment portion 212 is used for matching the rounded equilateral triangle shaped root of the tooth analogue for the upper central incisors. This rounded equilateral triangle shaped distal end 236 is one of the unique features of the present invention because it solves the problem of mismatching between the roots of the central incisors and the round or circular abutment shoulder provided by prior art dental implant systems. The smaller profile of the present invention rounded equilateral triangle distal end also allows two tooth analogues to be positioned at a desired or required close distance.

Referring to FIG. 16, there is shown at 310 an exploded view of still another alternative embodiment of the present invention anatomical restoration dental implant system. In this embodiment, the small bolt member 18, the abutment head 16 and the large bolt member 14 are identical to the parts shown in FIG. 2, and the description thereof will not be repeated and only the modified components will be described in detail. This embodiment shows a rounded isosceles triangle shaped healing abutment 312 which is substituted for the rounded equilateral triangle shaped healing abutment 12 shown in FIG. 2.

Referring to FIGS. 17 through 20, there is shown at 312 the rounded isosceles triangle shaped healing abutment of the present invention. The healing abutment 312 has a generally divergent body 332 which has a smaller proximal end 334 and a larger distal end 336. The smaller proximal end 334 is circular shaped, whereas the larger distal end 336 is rounded isosceles triangle shaped. The divergent body 332 also has a stepped interior bore 338 which extends from the distal end 336 to the proximal end 334. The divergent body 332 further has an intermediate shoulder 340 for accommodating the gingival tissues which surround the patient's jawbone. The intermediate shoulder 340 has a lingual-side portion 342 which is at a higher level and flush with the distal end 336 of the divergent body 332, a facial-side portion 344 which is at a lower level and adjacent to the proximal end 334 of the divergent body 332, and two opposite interproximal-side portions 346 and 348 which are gradually changing from the higher level at the lingual-side portion 342 to the lower level at the facial-side portion 344. The larger distal end 336 of the healing abutment 312 further comprises two opposite indents 350 and 352 which are adaptable with a dental forceps for orienting the healing abutment 312.

Particularly referring to FIG. 18, an isosceles triangle circumscribing the distal end 336 of the healing abutment 312 is shown in dotted lines to illustrate that the distal end 336 of the healing abutment 312 has a rounded isosceles triangle shape.

Referring to FIG. 20, there is shown a cross-sectional view of the healing abutment 312 of the present invention. There is a mating interface at the exposed end of the implant fixture and a complementary mating interface at the smaller proximal end 334 of the healing abutment 312 for orienting and aligning the healing abutment 312. The mating interface at the exposed end of the implant fixture is a hexagonal lip and the complementary mating interface at the smaller proximal end 334 of the healing abutment 312 is a hexagonal recess 354. It will be appreciated that at the smaller proximal end 334 of the healing abutment 312 is not limited to the hexagonal recess 354 as shown in FIG. 19. It is also within the spirit and scope of the present invention to utilize a circular recess provided at the smaller proximal end 334 of the healing abutment 312 for matching a complementary circular lip at the exposed end of the dental implant fixture.

The facial-side portion 344 of the healing abutment 312 accommodates the contour of the gingival tissue at the facial side of the patient. The lingual-side portion 342 of the healing abutment 312 accommodates the contour of the gingival tissue at the lingual side of the patient.

It is noted that the rounded isosceles triangle shaped distal end 336 of the healing abutment 312 is used for matching the rounded isosceles triangle shaped root of the tooth analogue for the lower lateral incisors and the upper lateral incisors. This rounded isosceles triangle shaped distal end 336 is one of the unique features of the present invention because it solves the problem of mismatching between the roots of the lower lateral incisors, the upper lateral incisors, and the round or circular abutment shoulder provided by prior art dental implant systems. The smaller profile of the present invention rounded isosceles triangle distal end also allows two tooth analogues to be positioned at a desired or required close distance.

Referring to FIG. 21, there is shown at 410 a further alternative embodiment of the present invention anatomical restoration dental implant system. In this embodiment, the healing abutment 312 is identical to the one shown in FIGS. 16 through 20 and the integral matching abutment member 116 is identical to the one shown in FIGS. 8 and 9. Since it assembles and functions the same as previously described above, the description thereof will not be repeated.

Figure 22:
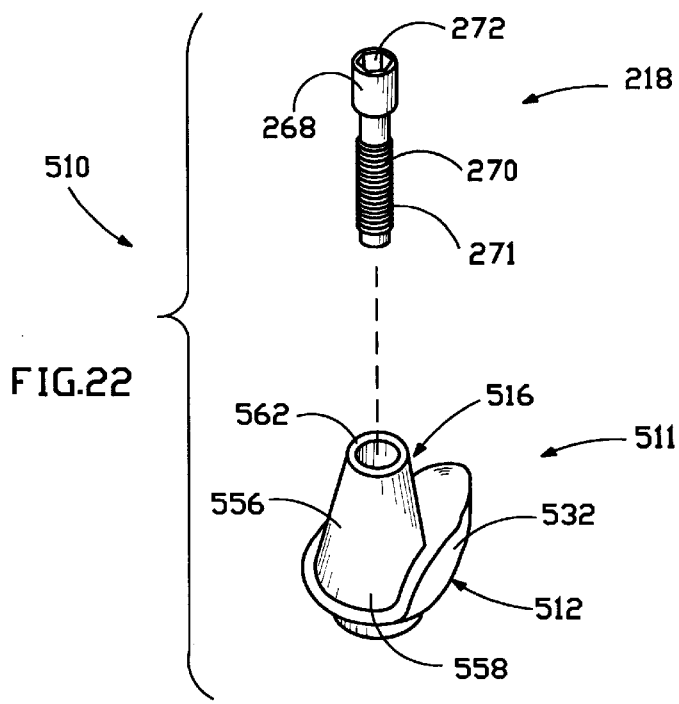
FIG. 22 is an exploded perspective view of another further alternative embodiment of the present invention anatomical restoration dental implant system, showing an integral member with a rounded isosceles triangle shaped healing abutment portion and a matching abutment portion.
Figure 23:
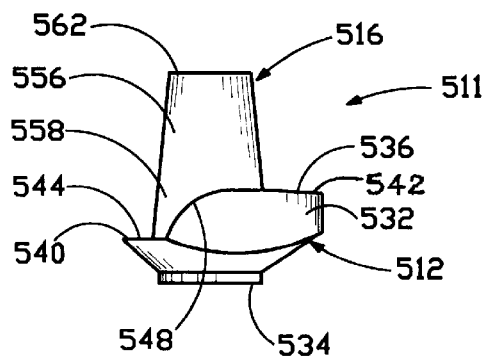
FIG. 23 is a side elevational view of the present invention integral member shown in FIG. 22.

Referring to FIG. 22, there is shown at 510 an exploded perspective view of another further alternative embodiment of the present invention anatomical restoration dental implant system which is attachable to an anatomical restoration dental implant fixture which is embedded into a patient's jawbone and has an exposed open end with inner screw threads (see FIG. 11). The dental implant system 510 can be made from an integral member 511 and a bolt member 218. Since the bolt member 218 is identical to the one shown in FIG. 10, the description thereof will not be repeated.

Referring to FIGS. 23 through 26, there is shown at 511 the integral member. The integral member 511 comprises a healing abutment portion 512 and a matching abutment head portion 516. The healing abutment portion 512 has a generally divergent body 532 which has a smaller proximal end 534 and a larger distal end 536. The smaller proximal end 534 is circular shaped, whereas the larger distal end 536 is rounded isosceles triangle shaped. The divergent body 532 also has a stepped interior bore 538 which extends from the distal end 536 to the proximal end 534. The divergent body 532 further has an intermediate shoulder 540 for accommodating the gingival tissues 5 and 7 (see FIG. 11) which surround the patient's jawbone 15. The intermediate shoulder 540 has a lingual-side 542 which is at a higher level and flush with the distal end 536 of the divergent body 532, a facial-side 544 which is at a lower level and adjacent to the proximal end 534 of the divergent body 532, and two opposite interproximal-sides 546 and 548 which are gradually changing from the higher level to the lower level. There is a mating interface at the exposed end 11 of the implant fixture 9 and a complementary mating interface at the smaller proximal end 534 of the healing abutment portion 512 for orienting and aligning the integral member 511. The mating interface at the exposed end of the implant fixture is a hexagonal lip and the complementary mating interface at the smaller proximal end 534 of the healing abutment portion 512 is a hexagonal recess 554.

Figure 25:
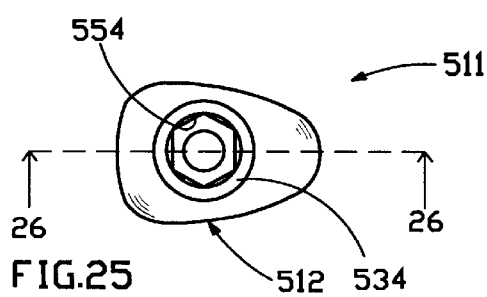
FIG. 25 is a bottom plan view of the present invention integral member shown in FIG. 22.
Figure 26:
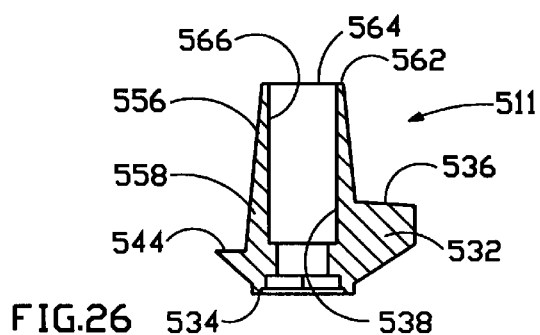
FIG. 26 is a cross-sectional view taken along line 26—26 of FIG. 25.

It will be appreciated that the smaller proximal end 534 of the healing abutment portion 512 is not limited to the hexagonal recess 554 as shown in FIG. 25. It is also within the spirit and scope of the present invention to utilize a circular recess provided at the smaller proximal end 534 of the healing abutment portion 512 for matching a complementary circular lip at the exposed end of the dental implant fixture.

Figure 24:
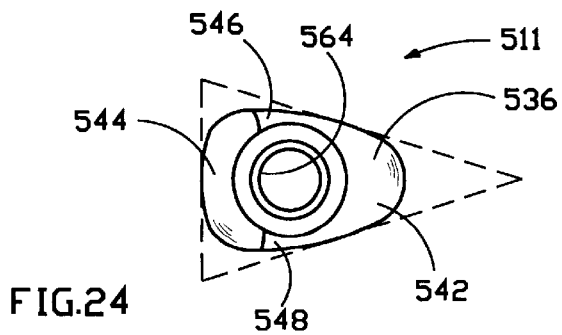
FIG. 24 is a top plan view of the present invention integral member shown in FIG. 22.

Particularly referring to FIG. 24, an isosceles triangle circumscribing the distal end 536 of the healing abutment portion 512 is shown in dotted lines to illustrate that the distal end 536 of the healing abutment portion 512 has a rounded isosceles triangle shape.

Referring to FIGS. 23 through 26, the matching abutment head portion 516 is used for supporting a tooth analogue. The abutment head portion 516 has a generally frusto-conical shaped body 556. The frusto-conical shaped body 556 has a larger proximal end 558 which is integrally connected to the larger distal end 536 of the healing abutment portion 512, a smaller distal end 562 with a circular opening 564, and a stepped interior bore 566 which extends from the circular opening 564 to the smaller proximal end 534 of the healing abutment portion 512.

The facial-side 544 of the healing abutment portion 512 accommodates the contour of the gingival tissue at the facial side of the patient. The lingual-side 542 of the healing abutment portion 512 accommodates the contour of the gingival tissue at the lingual side of the patient.

It is noted that the rounded isosceles triangle shaped distal end 536 of the healing abutment portion 512 is used for matching the rounded isosceles triangle shaped root of the tooth analogue for the lower lateral incisors and the upper lateral incisors. This rounded isosceles triangle shaped distal end 536 is one of the unique features of the present invention because it solves the problem of mismatching between the roots of the lower lateral incisors, the upper lateral incisors, and the round or circular abutment shoulder provided by prior art dental implant systems. The smaller profile of the present invention rounded isosceles triangle distal end also allows two tooth analogues to be positioned at a desired or required close distance.

Referring to FIG. 27, there is shown at 610 an exploded view of still a further alternative embodiment of the present invention anatomical restoration dental implant system. In this embodiment, the small bolt member 18, the abutment head 16 and the large bolt member 14 are identical to the parts shown in FIG. 2, and the description thereof will not be repeated and only the modified components will be described in detail. This embodiment shows an elliptical healing abutment 612 which is substituted for the rounded equilateral triangle shaped healing abutment 12 shown in FIG. 2.

Referring to FIGS. 28 through 31, there is shown at 612 the elliptical shaped healing abutment of the present invention. The healing abutment 612 has a generally divergent body 632 which has a smaller proximal end 634 and a larger distal end 636. The smaller proximal end 634 is circular shaped, whereas the larger distal end 636 is elliptical shaped. The divergent body 632 also has a stepped interior bore 638 which extends from the distal end 636 to the proximal end 634. The divergent body 632 further has an intermediate shoulder 640 for accommodating the gingival tissues which surround the patient's jawbone. The intermediate shoulder 640 has a lingual-side portion 642 which is at a higher level and flush with the distal end 636 of the divergent body 632, a facial-side portion 644 which is at a lower level and adjacent to the proximal end 634 of the divergent body 632, and two opposite interproximal-side portions 646 and 648 which are gradually changing from the higher level at the lingual-side portion 642 to the lower level at the facial-side portion 644. The larger distal end 636 of the healing abutment 612 further comprises two opposite indents 650 and 652 which are adaptable with a dental forceps for orienting the healing abutment 612.

Referring to FIG. 31, there is shown a cross-sectional view of the healing abutment 612 of the present invention. There is a mating interface at the exposed end of the implant fixture and a complementary mating interface at the smaller proximal end 634 of the healing abutment 612 for orienting and aligning the healing abutment 612. The mating interface at the exposed end of the implant fixture is a hexagonal lip and the complementary mating interface at the smaller proximal end 634 of the healing abutment 612 is a hexagonal recess 654. It will be appreciated that at the smaller proximal end of the healing abutment 612 is not limited to the hexagonal recess 654 as shown in FIG. 30. It is also within the spirit and scope of the present invention to utilize a circular recess provided at the smaller proximal end 634 of the healing abutment 612 for matching a complementary circular lip at the exposed end of the dental implant fixture.

The facial-side portion 644 of the healing abutment 612 accommodates the contour of the gingival tissue at the facial side of the patient. The lingual-side portion 642 of the healing abutment 612 accommodates the contour of the gingival tissue at the lingual side of the patient.

It is noted that the elliptical shaped distal end 636 of the healing abutment 612 is used for matching the elliptical root of the tooth analogue. This elliptical shaped distal end 636 is one of the unique features of the present invention because it solves the problem of mismatching between the roots of the tooth analogue, which is often oval or elliptical, and the round or circular abutment shoulder provided by prior art dental implant systems. The smaller profile of the present invention elliptical shaped distal end also allows two tooth analogues to be positioned at a desired or required close distance.

Referring to FIG. 32, there is shown at 710 an additional alternative embodiment of the present invention anatomical restoration dental implant system. In this embodiment, the healing abutment 612 is identical to the one shown in FIGS. 27 through 31 and the integral matching abutment member 116 is identical to the one shown in FIGS. 8 and 9. Since it assembles and functions the same as previously described above, the description thereof will not be repeated.

Referring to FIG. 33, there is shown at 810 an exploded perspective view of another additional alternative embodiment of the present invention anatomical restoration dental implant system which is attachable to an anatomical restoration dental implant fixture which is embedded into a patient's jawbone and has an exposed open end with inner screw threads (see FIG. 11). The dental implant system 810 can be made from an integral member 811 and a bolt member 218. Since the bolt member 218 is identical to the one shown in FIG. 10, the description thereof will not be repeated.

Referring to FIGS. 34 through 37, there is shown at 811 the integral member. The integral member 811 comprises a healing abutment portion 812 and a matching abutment head portion 816. The healing abutment portion 812 has a generally divergent body 832 which has a smaller proximal end 834 and a larger distal end 836. The smaller proximal end 834 is circular shaped, whereas the larger distal end 836 is elliptical shaped. The divergent body 832 also has a stepped interior bore 838 which extends from the distal end 836 to the proximal end 834. The divergent body 832 further has an intermediate shoulder 840 for accommodating the gingival tissues 5 and 7 (see FIG. 11) which surround the patient's jawbone 15. The intermediate shoulder 840 has a lingual-side 842 which is at a higher level and flush with the distal end 836 of the divergent body 832, a facial-side 844 which is at a lower level and adjacent to the proximal end 834 of the divergent body 832, and two opposite interproximal-sides 846 and 848 which are gradually changing from the higher level to the lower level. There is a mating interface at the exposed end of the implant fixture and a complementary mating interface at the smaller proximal end 834 of the healing abutment portion 812 for orienting and aligning the integral member 811. The mating interface at the exposed end of the implant fixture is a hexagonal lip and the complementary mating interface at the smaller proximal end 834 of the healing abutment portion 812 is a hexagonal recess 854.

It will be appreciated that at the smaller proximal end 834 of the healing abutment portion 812 is not limited to the hexagonal recess 854 as shown in FIG. 36. It is also within the spirit and scope of the present invention to utilize a circular recess provided at the smaller proximal end 834 of the healing abutment portion 812 for matching a complementary circular lip at the exposed end of the dental implant fixture.

Referring to FIGS. 34 through 37, the matching abutment head portion 816 is used for supporting a tooth analogue. The abutment head portion 816 has a generally frusto-conical shaped body 856. The frusto-conical shaped body 856 has a larger proximal end 858 which is integrally connected to the larger distal end 836 of the healing abutment portion 812, a smaller distal end 862 with a circular opening 864, and a stepped interior bore 866 which extends from the circular opening 864 to the smaller proximal end 834 of the healing abutment 812.

The facial-side 844 of the healing abutment portion 812 accommodates the contour of the gingival tissue at the facial side of the patient. The lingual-side 842 of the healing abutment 812 accommodates the contour of the gingival tissue at the lingual side of the patient.

It is noted that the elliptical shaped distal end 836 of the healing abutment head portion 812 is used for matching the elliptical root of the tooth analogue. This elliptical shaped distal end 836 is one of the unique features of the present invention because it solves the problem of mismatching between the roots of the tooth analogue, which is often oval or elliptical, and the round or circular abutment shoulder provided by prior art dental implant systems. The smaller profile of the present invention elliptical shaped distal end also allows two tooth analogues to be positioned at a desired or required close distance.

Defined in detail, the present invention is an apparatus attachable to an anatomical restoration dental implant fixture which is embedded into a patient's jawbone and has an exposed open end with inner screw threads, the apparatus comprising: (a) a healing abutment having a generally divergent body with a smaller proximal end and a larger distal end, the divergent body also having an interior bore extending from the distal end to the proximal end, the divergent body further having an intermediate shoulder for accommodating the gingival tissues surrounding the patient's jawbone, the shoulder having a lingual-side portion having a higher level which is flush with the distal end of the divergent body, a facial-side portion having a lower level close to the proximal end, and two opposite interproximal-side portions gradually changing from the higher level to the lower level; (b) a first bolt member having a head segment and an elongated shaft segment, the head segment having an exposed open end with inner screw threads, the shaft segment having outer screw threads; (c) the shaft segment of the first bolt member being longer than the interior bore of the healing abutment, such that after the shaft segment of the bolt member extends through the interior bore of the healing abutment from the proximal end of the healing abutment, there is still a substantial portion of the outer screw threads of the shaft segment of the first bolt member which can be threadably engaged with the implant fixture for fastening the healing abutment to the exposed end of the implant fixture, where the head segment of the first bolt member extends above the distal end of the healing abutment; (d) a matching abutment head for supporting a tooth analogue and having a generally frusto-conical shaped body, the frusto-conical shaped body having a larger proximal end with a widened socket, a smaller distal end with a circular opening, and an interior bore extending from the widened socket to the circular opening; (e) the larger proximal end of the frusto-conical shaped body of the abutment head installed on the distal end of the healing abutment, such that the widened socket matches the head segment of the first bolt member; and (f) a second bolt member having a circular shaped head segment and a shaft segment with outer screw threads, the head segment having an internal opening for adapting a driving tool such that the second bolt member extends through the interior bore of the abutment head from the circular opening and the outer screw threads threadedly engage the inner screw threads of the exposed open end of the head segment of the first bolt member, thereby securing the abutment head to the healing abutment; (g) whereby the facial-side portion of the healing abutment accommodates the contour of the gingival tissue at the facial side of the patient and the lingual-side portion of the healing abutment accommodates the contour of the gingival tissue at the lingual side of the patient.

Defined broadly, the present invention is an apparatus attachable to an anatomical restoration dental implant fixture which is embedded into a patient's jawbone and has an exposed open end with inner screw threads, the apparatus comprising: (a) a generally divergent body having a proximal end and a distal end, the divergent body also having an interior bore extending from the distal end to the proximal end, the divergent body further having an intermediate shoulder for accommodating the gingival tissues surrounding the patient's jawbone, the shoulder having a lingual-side portion having a higher level which is flush with the distal end of the divergent body, a facial-side portion having a lower level close to the proximal end, and two opposite interproximal-side portions gradually changing from the higher level to the lower level; (b) a first bolt member being longer than the interior bore of the divergent body, such that after the first bolt member extends through the interior bore of the divergent body from the proximal end of the divergent body, the first bolt member securely fastened the divergent body to the exposed end of the implant fixture; (c) an abutment head for supporting a tooth analogue and having a generally frusto-conical shaped body, the frusto-conical shaped body having a proximal end, a distal end, and an interior bore extending from the proximal end to the distal end, the proximal end of the frusto-conical shaped body installed on the distal end of the divergent body; and (d) a second bolt member extending through the interior bore of the abutment head from the distal end such that the second bolt member securely fastens the abutment head to the divergent body; (e) whereby the facial-side portion of the divergent body accommodates the contour of the gingival tissue at the facial side of the patient and the lingual-side portion of the divergent body accommodates the contour of the gingival tissue at the lingual side of the patient.

Defined alternatively in detail, the present invention is an apparatus attachable to an anatomical restoration dental implant fixture which is embedded into a patient's jawbone and has an exposed open end with inner screw threads, the apparatus comprising: (a) a healing abutment having a generally divergent body with a smaller proximal end and a larger distal end, the divergent body also having an interior bore extending from the distal end to the proximal end, the divergent body further having an intermediate shoulder for accommodating the gingival tissues surrounding the patient's jawbone, the shoulder having a lingual-side portion having a higher level which is flush with the distal end of the divergent body, a facial-side portion having a lower level close to the proximal end, and two opposite interproximal-side portions gradually changing from the higher level to the lower level; (b) a matching abutment member further comprising, (i) a proximal bolt portion having a head segment and an elongated shaft segment, the shaft segment having outer screw threads, the shaft segment being longer than the interior bore of the healing abutment, such that after the shaft segment extends through the interior bore of the healing abutment from the proximal end of the healing abutment, there is still a substantial portion of the outer screw threads of the shaft segment which can be threadably engages with the implant fixture for fastening the healing abutment to the exposed end of the implant fixture, and (ii) a generally frusto-conical shaped distal head portion for supporting a tooth analogue and having a larger proximal end and a smaller distal end, the larger proximal end integrally connected to the head segment of the proximal bolt portion;

(c) whereby the facial-side portion of the healing abutment accommodates the contour of the gingival tissue at the facial side of the patient and the lingual-side portion of the healing abutment accommodates the contour of the gingival tissue at the lingual side of the patient.

Defined alternatively broadly, the present invention is an apparatus attachable to an anatomical restoration dental implant fixture which is embedded into a patient's jawbone and has an exposed open end with inner screw threads, the apparatus comprising: (a) a generally divergent body having a proximal end and a distal end, the divergent body also having an interior bore extending from the distal end to the proximal end, the divergent body further having an intermediate shoulder for accommodating the gingival tissues surrounding the patient's jawbone, the shoulder having a lingual-side portion having a higher level which is flush with the distal end of the divergent body, a facial-side portion having a lower level close to the proximal end, and two opposite interproximal-side portions gradually changing from the higher level to the lower level; (b) an abutment member further comprising, (i) a proximal bolt portion being longer than the interior bore of the divergent body, such that after the proximal bolt portion extends through the interior bore of the divergent body from the proximal end of the divergent body, the proximal bolt portion threadably engaged with the implant fixture for fastening the divergent body to the exposed end of the implant fixture, and (ii) a generally frusto-conical shaped distal head portion for supporting a tooth analogue and integrally connected to the proximal bolt portion;

(c) whereby the facial-side portion of the divergent body accommodates the contour of the gingival tissue at the facial side of the patient and the lingual-side portion of the divergent body accommodates the contour of the gingival tissue at the lingual side of the patient.

Defined also alternatively in detail, the present invention is an apparatus attachable to an anatomical restoration dental implant fixture which is embedded into a patient's jawbone and has an exposed open end with inner screw threads, the apparatus comprising: (a) an integral member further comprising, (i) a healing abutment portion having a generally divergent body with a larger distal end and a smaller proximal end, the divergent body also having an interior bore extending from the distal end to the proximal end, the divergent body further having an intermediate shoulder for accommodating the gingival tissues surrounding the patient's jawbone, the shoulder having a lingual-side having a higher level which is flush with the distal end of the divergent body, a facial-side having a lower level close to the proximal end, and two opposite interproximal-sides gradually changing from the higher level to the lower level, (ii) a matching abutment portion for supporting a tooth analogue and having a generally frusto-conical shaped body, the frusto-conical shaped body having a larger proximal end integrally connected to the larger distal end of the healing abutment portion, a smaller distal end with a circular opening, and an interior bore extending from the circular opening to the smaller proximal end of the healing abutment portion; and (b) a bolt member having a circular shaped head segment and an elongated shaft segment with outer screw threads, the head segment having an internal opening for adapting a driving tool such that the bolt member extends through the interior bores of the healing abutment portion and the matching abutment portion and extends from the proximal end of the healing abutment portion and the outer screw threads threadedly engaged the inner screw threads of the exposed open end of the implant fixture for fastening the integral member to the implant fixture; (c) whereby the facial-side of the healing abutment portion accommodates the contour of the gingival tissue at the facial side of the patient and the lingual-side of the healing abutment portion accommodates the contour of the gingival tissue at the lingual side of the patient.

Defined also alternatively broadly, the present invention is an apparatus attachable to an anatomical restoration dental implant fixture which is embedded into a patient's jawbone and has an exposed open end with inner screw threads, the apparatus comprising: (a) an integral member further comprising, (i) a generally divergent body having a proximal end and a distal end, the divergent body also having an interior bore extending from the distal end to the proximal end, the divergent body further having an intermediate shoulder for accommodating the gingival tissues surrounding the patient's jawbone, the shoulder having a lingual-side having a higher level which is flush with the distal end of the divergent body, a facial-side having a lower level close to the proximal end, and two opposite interproximal-sides gradually changing from the higher level to the lower level, (ii) a matching abutment portion for supporting a tooth analogue and having a generally frusto-conical shaped body, the frusto-conical shaped body having a proximal end integrally connected to the distal end of the divergent body, a distal end, and an interior bore extending from the distal end to the proximal end of the divergent body; and (b) a bolt member extending through the interior bores of the abutment portion and the divergent body from the proximal end of the divergent body such that the bolt member threadedly engaged the inner screw threads of the exposed open end of the implant fixture for fastening the integral member to the implant fixture; (c) whereby the facial-side of the divergent body accommodates the contour of the gingival tissue at the facial side of the patient and the lingual-side of the divergent body accommodates the contour of the gingival tissue at the lingual side of the patient.

Defined further alternatively in detail, the present invention is an apparatus attachable to an anatomical restoration dental implant fixture which is embedded into a patient's jawbone and has an exposed open end with inner screw threads, the apparatus comprising: (a) a healing abutment having a generally divergent body with a smaller proximal end and a larger distal end, the divergent body also having an interior bore extending from the distal end to the proximal end, the divergent body further having an intermediate shoulder for accommodating the gingival tissues surrounding the patient's jawbone, the shoulder having a lingual-side portion having a higher level which is flush with the distal end of the divergent body, a facial-side portion having a lower level close to the proximal end, and two opposite interproximal-side portions gradually changing from the higher level to the lower level; and (b) a bolt member having a head segment and an elongated shaft segment, the head segment having an exposed open end with inner screw threads, the shaft segment having outer screw threads, the shaft segment being longer than the interior bore of the healing abutment, such that after the shaft segment extends through the interior bore of the healing abutment from the proximal end of the healing abutment, there is still a substantial portion of the outer screw threads of the shaft segment which can be threadably engaged with the implant fixture for fastening the healing abutment to the exposed end of the implant fixture; (c) whereby the facial-side portion of the healing abutment accommodates the contour of the gingival tissue at the facial side of the patient and the lingual-side portion of the healing abutment accommodates the contour of the gingival tissue at the lingual side of the patient.

Defined further alternatively broadly, the present invention is an apparatus attachable to an anatomical restoration dental implant fixture which is embedded into a patient's jawbone and has an exposed open end with inner screw threads, the apparatus comprising: (a) a generally divergent body having a proximal end and a distal end, the divergent body also having an interior bore extending from the distal end to the proximal end, the divergent body further having an intermediate shoulder for accommodating the gingival tissues surrounding the patient's jawbone, the shoulder having a lingual-side portion having a higher level which is flush with the distal end of the divergent body, a facial-side portion having a lower level close to the proximal end, and two opposite interproximal-side portions gradually changing from the higher level to the lower level; (b) whereby the facial-side portion of the divergent body accommodates the contour of the gingival tissue at the facial side of the patient and the lingual-side portion of the divergent body accommodates the contour of the gingival tissue at the lingual side of the patient.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. An apparatus attachable to an anatomical restoration dental implant fixture which is embedded into a patient's jawbone and has an exposed open end with inner screw threads, the apparatus comprising:

a. a healing abutment having a generally divergent body with a smaller proximal end and a larger distal end, the divergent body also having an interior bore extending from the distal end to the proximal end, the divergent body further having an intermediate shoulder for accommodating the gingival tissues surrounding the patient's jawbone, the shoulder having a lingual-side portion having a higher level which is flush with the distal end of the divergent body, a facial-side portion having a lower level close to the proximal end, and two opposite interproximal-side portions gradually changing from the higher level to the lower level, the lingual-side portion of said shoulder having a greater surface area than the facial-side portion of said shoulder;

b. a first bolt member having a head segment and an elongated shaft segment, the head segment having an exposed open end with inner screw threads, the shaft segment having outer screw threads;

c. said shaft segment of said first bolt member being longer than said interior bore of said healing abutment, such that after said shaft segment of said bolt member extends through said interior bore of said healing abutment from said proximal end of said healing abutment, there is still a substantial portion of said outer screw threads of said shaft segment of said first bolt member which can be threadably engaged with said implant fixture for fastening said healing abutment to said exposed end of said implant fixture, where said head segment of said first bolt member extends above said distal end of said healing abutment;

d. a matching abutment head for supporting a tooth analogue and having a generally frusto-conical shaped body, the frusto-conical shaped body having a larger proximal end with a widened socket, a smaller distal end with a circular opening, and an interior bore extending from the widened socket to the circular opening;

e. said larger proximal end of said frusto-conical shaped body of said abutment head installed on said distal end of said healing abutment, such that said widened socket matches said head segment of said first bolt member; and f. a second bolt member having a circular shaped head segment and a shaft segment with outer screw threads, the head segment having an internal opening for adapting a driving tool such that the second bolt member extends through said interior bore of said abutment head from said circular opening and the outer screw threads threadedly engage said inner screw threads of said exposed open end of said head segment of said first bolt member, thereby securing said abutment head to said healing abutment;

g. whereby said facial-side portion of said healing abutment accommodates the contour of the gingival tissue at the facial side of said patient and said lingual-side portion of said healing abutment accommodates the contour of the gingival tissue at the lingual side of said patient.

2. The apparatus in accordance with claim 1 further comprising a mating interface at said exposed end of said implant fixture and a complementary mating interface at said smaller proximal end of said healing abutment for orienting and aligning said healing abutment.

3. The apparatus in accordance with claim 2 wherein said mating interface at said exposed end of said implant fixture is a hexagonal lip and said complementary mating interface at said smaller proximal end of said healing abutment is a hexagonal recess.

4. The apparatus in accordance with claim 1 wherein said larger distal end of said healing abutment further comprises two opposite indents adaptable with a dental forceps for orienting said healing abutment.

5. The apparatus in accordance with claim 1 wherein said head segment of said first bolt member has means cooperable with a driving tool.

6. The apparatus in accordance with claim 1 wherein said widened socket at said larger proximal end of said frusto-conical shaped body of said abutment head is a hexagonal recess.

7. The apparatus in accordance with claim 6 wherein said head segment of said first bolt member is a hexagonal lip which matches said hexagonal recess at said frusto-conical shaped body of said abutment head.

8. The apparatus in accordance with claim 1 wherein said larger distal end of said healing abutment is generally a rounded equilateral triangle shape.

9. The apparatus in accordance with claim 1 wherein said larger distal end of said healing abutment is generally a rounded isosceles triangle shape.

10. The apparatus in accordance with claim 1 wherein said larger distal end of said healing abutment is generally an elliptical shape.

11. An apparatus attachable to an anatomical restoration dental implant fixture which is embedded into a patient's jawbone and has an exposed open end with inner screw threads, the apparatus comprising:

a. a generally divergent body having a proximal end and a distal end, the divergent body also having an interior bore extending from the distal end to the proximal end, the divergent body further having an intermediate shoulder for accommodating the gingival tissues surrounding the patient's jawbone, the shoulder having a lingual-side portion having a higher level which is flush with the distal end of the divergent body, a facial-side portion having a lower level close to the proximal end, and two opposite interproximal-side portions gradually changing from the higher level to the lower level, the lingual-side portion of said shoulder having a greater surface area than the facial-side portion of said shoulder;

b. a first bolt member being longer than said interior bore of said divergent body, such that after the first bolt member extends through said interior bore of said divergent body from said proximal end of said divergent body, the first bolt member securely fastens said divergent body to said exposed end of said implant fixture;

c. an abutment head for supporting a tooth analogue and having a generally frusto-conical shaped body, the frusto-conical shaped body having a proximal end, a distal end, and an interior bore extending from the proximal end to the distal end, the proximal end of the frusto-conical shaped body installed on said distal end of said divergent body; and d. a second bolt member extending through said interior bore of said abutment head from said distal end such that the second bolt member securely fastens said abutment head to said divergent body;

e. whereby said facial-side portion of said divergent body accommodates the contour of the gingival tissue at the facial side of said patient and said lingual-side portion of said divergent body accommodates the contour of the gingival tissue at the lingual side of said patient.

12. The apparatus in accordance with claim 11 further comprising a mating interface at said exposed end of said implant fixture and a complementary mating interface at said proximal end of said divergent body for orienting and aligning said divergent body.

13. The apparatus in accordance with claim 11 wherein said distal end of said divergent body further comprises two opposite indents adaptable with a dental forceps for orienting said divergent body.

14. The apparatus in accordance with claim 11 wherein said head segments of said first and second bolt members have means cooperable with a driving tool.

15. The apparatus in accordance with claim 11 wherein said distal end of said divergent body is generally a rounded equilateral triangle shape.

16. The apparatus in accordance with claim 11 wherein said distal end of said divergent body is generally a rounded isosceles triangle shape.

17. The apparatus in accordance with claim 11 wherein said distal end of said divergent body is generally an elliptical shape.

18. An apparatus attachable to an anatomical restoration dental implant fixture which is embedded into a patient's jawbone and has an exposed open end with inner screw threads, the apparatus comprising:

a. a healing abutment having a generally divergent body with a smaller proximal end and a larger distal end, the divergent body also having an interior bore extending from the distal end to the proximal end, the divergent body further having an intermediate shoulder for accommodating the gingival tissues surrounding the patient's jawbone, the shoulder having a lingual-side portion having a higher level which is flush with the distal end of the divergent body, a facial-side portion having a lower level close to the proximal end, and two opposite interproximal-side portions gradually changing from the higher level to the lower level, the lingual-side portion of said shoulder having a greater surface area than the facial-side portion of said shoulder;

b. a matching abutment member further comprising,
  (i) a proximal bolt portion having a head segment and an elongated shaft segment, the shaft segment having outer screw threads, the shaft segment being longer than said interior bore of said healing abutment, such that after the shaft segment extends through said interior bore of said healing abutment from said proximal end of said healing abutment, there is still a substantial portion of the outer screw threads of the shaft segment which can be threadably engaged with said implant fixture for fastening said healing abutment to said exposed end of said implant fixture, and
  (ii) a generally frusto-conical shaped distal head portion for supporting a tooth analogue and having a larger proximal end and a smaller distal end, the larger proximal end integrally connected to said head segment of said proximal bolt portion;
c. whereby said facial-side portion of said healing abutment accommodates the contour of the gingival tissue at the facial side of said patient and said lingual-side portion of said healing abutment accommodates the contour of the gingival tissue at the lingual side of said patient.

19. The apparatus in accordance with claim 18 further comprising a mating interface at said exposed end of said implant fixture and a complementary mating interface at said smaller proximal end of said healing abutment for orienting and aligning said healing abutment.

20. The apparatus in accordance with claim 19 wherein said mating interface at said exposed end of said implant fixture is a hexagonal lip and said complementary mating interface at said smaller proximal end of said healing abutment is a hexagonal recess.

21. The apparatus in accordance with claim 18 wherein said larger distal end of said healing abutment further comprises two opposite indents adaptable with a dental forceps for orienting said healing abutment.

22. The apparatus in accordance with claim 18 wherein said smaller distal end of said frusto-conical shaped distal head portion of said abutment member has a notch to accommodate a driving tool such as a screw driver for rotating said abutment member.

23. The apparatus in accordance with claim 18 wherein said larger distal end of said healing abutment is generally a rounded equilateral triangle shape.

24. The apparatus in accordance with claim 18 wherein said larger distal end of said healing abutment is generally a rounded isosceles triangle shape.

25. The apparatus in accordance with claim 18 wherein said larger distal end of said healing abutment is generally an elliptical shape.

26. An apparatus attachable to an anatomical restoration dental implant fixture which is embedded into a patient's jawbone and has an exposed open end with inner screw threads, the apparatus comprising:
a. a generally divergent body having a proximal end and a distal end, the divergent body also having an interior bore extending from the distal end to the proximal end, the divergent body further having an intermediate shoulder for accommodating the gingival tissues surrounding the patient's jawbone, the shoulder having a lingual-side portion having a higher level which is flush with the distal end of the divergent body, a facial-side portion having a lower level close to the proximal end, and two opposite interproximal-side portions gradually changing from the higher level to the lower level, the lingual-side portion of said shoulder having a greater surface area than the facial-side portion of said shoulder;

b. an abutment member further comprising,
  (i) a proximal bolt portion being longer than said interior bore of said divergent body, such that after the proximal bolt portion extends through said interior bore of said divergent body from said proximal end of said divergent body, the proximal bolt portion threadably engages with said implant fixture for fastening said divergent body to said exposed end of said implant fixture, and
  (ii) a generally frusto-conical shaped distal head portion for supporting a tooth analogue and integrally connected to said proximal bolt portion;
c. whereby said facial-side portion of said divergent body accommodates the contour of the gingival tissue at the facial side of said patient and said lingual-side portion of said divergent body accommodates the contour of the gingival tissue at the lingual side of said patient.

27. The apparatus in accordance with claim 26 further comprising a mating interface at said exposed end of said implant fixture and a complementary mating interface at said proximal end of said divergent body for orienting and aligning said divergent body.

28. The apparatus in accordance with claim 26 wherein said distal end of said divergent body further comprises two opposite indents adaptable with a dental forceps for orienting said divergent body.

29. The apparatus in accordance with claim 26 wherein said frusto-conical shaped distal head portion of said abutment member further comprises a distal end with a notch to accommodate a driving tool such as a screw driver for rotating said abutment member.

30. The apparatus in accordance with claim 26 wherein said distal end of said divergent body is generally a rounded equilateral triangle shape.

31. The apparatus in accordance with claim 26 wherein said distal end of said divergent body is generally a rounded isosceles triangle shape.

32. The apparatus in accordance with claim 26 wherein said distal end of said divergent body is generally an elliptical shape.

33. An apparatus attachable to an anatomical restoration dental implant fixture which is embedded into a patient's jawbone and has an exposed open end with inner screw threads, the apparatus comprising:
a. an integral member further comprising,
  (i) a healing abutment portion having a generally divergent body with a larger distal end and a smaller proximal end, the divergent body also having an interior bore extending from the distal end to the proximal end, the divergent body further having an intermediate shoulder for accommodating the gingival tissues surrounding the patient's jawbone, the shoulder having a lingual-side portion having a higher level which is flush with the distal end of the divergent body, a facial-side portion having a lower level close to the proximal end, and two opposite interproximal-sides gradually changing from the higher level to the lower level, the lingual-side portion of said shoulder having a greater surface area than the facial-side portion of said shoulder;
  (ii) a matching abutment portion for supporting a tooth analogue and having a generally frusto-conical shaped body, the frusto-conical shaped body having a larger proximal end integrally connected to said larger distal end of said healing abutment portion, a smaller distal end with a circular opening, and an interior bore extending from the circular opening to said smaller proximal end of said healing abutment portion; and b. a bolt member having a circular shaped head segment and an elongated shaft segment with outer screw threads, the head segment having an internal opening for adapting a driving tool such that the bolt member extends through said interior bores of said healing abutment portion and said matching abutment portion and extending from said proximal end of said healing abutment portion and the outer screw threads threadedly engaged said inner screw threads of said exposed open end of said implant fixture for fastening said integral member to said implant fixture;

c. whereby said facial-side of said healing abutment portion accommodates the contour of the gingival tissue at the facial side of said patient and said lingual-side of said healing abutment portion accommodates the contour of the gingival tissue at the lingual side of said patient.

34. The apparatus in accordance with claim 33 further comprising a mating interface at said exposed end of said implant fixture and a complementary mating interface at said smaller proximal end of said healing abutment portion for orienting and aligning said integral member.

35. The apparatus in accordance with claim 34 wherein said mating interface at said exposed end of said implant fixture is a hexagonal lip and said complementary mating interface at said smaller proximal end of said healing abutment portion is a hexagonal recess.

36. The apparatus in accordance with claim 33 wherein said larger distal end of said healing abutment portion is generally a rounded equilateral triangle shape.

37. The apparatus in accordance with claim 33 wherein said larger distal end of said healing abutment portion is generally a rounded isosceles triangle shape.

38. The apparatus in accordance with claim 33 wherein said larger distal end of said healing abutment portion is generally an elliptical shape.

39. An apparatus attachable to an anatomical restoration dental implant fixture which is embedded into a patient's jawbone and has an exposed open end with inner screw threads, the apparatus comprising:

a. an integral member further comprising,
(i) a generally divergent body having a proximal end and a distal end, the divergent body also having an interior bore extending from the distal end to the proximal end, the divergent body further having an intermediate shoulder for accommodating the gingival tissues surrounding the patient's jawbone, the shoulder having a lingual-side portion having a higher level which is flush with the distal end of the divergent body, a facial-side portion having a lower level close to the proximal end, and two opposite interproximal-sides gradually changing from the higher level to the lower level, the lingual-side portion of said shoulder having a greater surface area than the facial-side portion of said shoulder;
(ii) a matching abutment portion for supporting a tooth analogue and having a generally frusto-conical shaped body, the frusto-conical shaped body having a proximal end integrally connected to said distal end of said divergent body, a distal end, and an interior bore extending from the distal end to said proximal end of said divergent body; and b. a bolt member extending through said interior bores of said abutment portion and said divergent body from said proximal end of said divergent body such that the bolt member threadedly engages said inner screw threads of said exposed open end of said implant fixture for fastening said integral member to said implant fixture;

c. whereby said facial-side of said divergent body accommodates the contour of the gingival tissue at the facial side of said patient and said lingual-side of said divergent body accommodates the contour of the gingival tissue at the lingual side of said patient.

40. The apparatus in accordance with claim 39 further comprising a mating interface at said exposed end of said implant fixture and a complementary mating interface at said proximal end of said divergent body for orienting and aligning said integral member.

41. The apparatus in accordance with claim 39 wherein said bolt member further comprises an open end for cooperable with a driving tool.

42. The apparatus in accordance with claim 39 wherein said distal end of said divergent body is generally a rounded equilateral triangle shape.

43. The apparatus in accordance with claim 39 wherein said distal end of said divergent body is generally a rounded isosceles triangle shape.

44. The apparatus in accordance with claim 39 wherein said distal end of said divergent body is generally an elliptical shape.

45. An apparatus attachable to an anatomical restoration dental implant fixture which is embedded into a patient's jawbone and has an exposed open end with inner screw threads, the apparatus comprising:

a. a healing abutment having a generally divergent body with a smaller proximal end and a larger distal end, the divergent body also having an interior bore extending from the distal end to the proximal end, the divergent body further having an intermediate shoulder for accommodating the gingival tissues surrounding the patient's jawbone, the shoulder having a lingual-side portion having a higher level which is flush with the distal end of the divergent body, a facial-side portion having a lower level close to the proximal end, and two opposite interproximal-side portions gradually changing from the higher level to the lower level, the lingual-side portion of said shoulder having a greater surface area than the facial-side portion of said shoulder; and b. a bolt member having a head segment and an elongated shaft segment, the head segment having an exposed open end with inner screw threads, the shaft segment having outer screw threads, the shaft segment being longer than said interior bore of said healing abutment, such that after the shaft segment extends through said interior bore of said healing abutment from said proximal end of said healing abutment, there is still a substantial portion of the outer screw threads of the shaft segment which can be threadably engaged with said implant fixture for fastening said healing abutment to said exposed end of said implant fixture;

c. whereby said facial-side portion of said healing abutment accommodates the contour of the gingival tissue at the facial side of said patient and said lingual-side portion of said healing abutment accommodates the contour of the gingival tissue at the lingual side of said patient.

46. The apparatus in accordance with claim 45 further comprising a matching abutment head for supporting a tooth analogue and having a frusto-conical shaped body, the frusto-conical shaped body having a larger proximal end with a widened socket, a smaller distal end with a circular opening, and an interior bore extending from the widened socket to the circular opening, the larger proximal end installed on said distal end of said healing abutment, such that the widened socket matches said head segment of said bolt member.

47. The apparatus in accordance with claim 45 further comprising another bolt member having a head segment and a shaft segment with outer screw threads, the head segment having an internal opening for adapting a driving tool such that the another bolt member extends through said interior bore of said abutment head from said circular opening at said smaller distal end of said frusto-conical shaped body of said abutment head and the outer screw threads threadedly engaged said inner screw threads of said exposed open end of said head segment of said bolt member, thereby securing said abutment head to said healing abutment.

48. The apparatus in accordance with claim 45 wherein said larger distal end of said healing abutment is generally a rounded equilateral triangle shape.

49. The apparatus in accordance with claim 45 wherein said larger distal end of said healing abutment is generally a rounded isosceles triangle shape.

50. The apparatus in accordance with claim 45 wherein said larger distal end of said healing abutment is generally an elliptical shape.

51. An apparatus attachable to an anatomical restoration dental implant fixture which is embedded into a patient's jawbone and has an exposed open end with inner screw threads, the apparatus comprising:

a. a generally divergent body having a proximal end and a distal end, the divergent body also having an interior bore extending from the distal end to the proximal end, the divergent body further having an intermediate shoulder for accommodating the gingival tissues surrounding the patient's jawbone, the shoulder having a lingual-side portion having a higher which is flush with the distal end of the divergent body, a facial-side portion having a lower level close to the proximal end, and two opposite interproximal-side portions gradually changing from the higher level to the lower level, the lingual-side portion of said shoulder having a greater surface area than the facial-side portion of said shoulder;

b. whereby said facial-side portion of said divergent body accommodates the contour of the gingival tissue at the facial side of said patient and said lingual-side portion of said divergent body accommodates the contour of the gingival tissue at the lingual side of said patient.

52. The apparatus in accordance with claim 51 further comprising a bolt member having a head segment and an elongated shaft segment, the head segment having an exposed open end with inner screw threads, the shaft segment having outer screw threads, the shaft segment being longer than said interior bore of said divergent body, such that after the shaft segment of the bolt member extends through said interior bore of said divergent body from said distal end of said divergent body, the outer screw threads of the shaft segment of the bolt member threadably engaged with said inner screw threads of said implant fixture for fastening said divergent body to said implant fixture.

53. The apparatus in accordance with claim 51 further comprising an abutment head for supporting a tooth analogue and having a frusto-conical shaped body, the frusto-conical shaped body having a proximal end with a widened socket, a distal end with a circular opening, and an interior bore extending from the widened socket to the circular opening, the proximal end installed on said distal end of said divergent body, such that the widened socket matches said head segment of said bolt member.

54. The apparatus in accordance with claim 51 further comprising another bolt member having a head segment and a shaft segment with outer screw threads, the head segment having an internal opening such that the another bolt member extends through said interior bore of said abutment head from said circular opening and the outer screw threads threadedly engaged said inner screw threads of said exposed open end of said head segment of said bolt member, thereby securing said abutment head to said divergent body.

55. The apparatus in accordance with claim 51 wherein said distal end of said divergent body is generally a rounded equilateral triangle shape.

56. The apparatus in accordance with claim 51 wherein said distal end of said divergent body is generally a rounded isosceles triangle shape.

57. The apparatus in accordance with claim 51 wherein said distal end of 'said divergent body is generally an elliptical shape.

* * * * *